US012491320B2

(12) United States Patent
Roiron

(10) Patent No.: US 12,491,320 B2
(45) Date of Patent: Dec. 9, 2025

(54) SYRINGE WITH A CONFORMABLE HANDLE

(71) Applicant: Jean-Francois Roiron, Paddington (AU)

(72) Inventor: Jean-Francois Roiron, Paddington (AU)

(73) Assignee: Jean-Francois Roiron, Paddington (AU)

( * ) Notice: Subject to any disclaimer, the term of this patent is extended or adjusted under 35 U.S.C. 154(b) by 0 days.

(21) Appl. No.: 18/865,355

(22) PCT Filed: Jun. 12, 2024

(86) PCT No.: PCT/AU2024/050612
§ 371 (c)(1),
(2) Date: Nov. 13, 2024

(87) PCT Pub. No.: WO2024/259473
PCT Pub. Date: Dec. 26, 2024

(65) Prior Publication Data

US 2025/0135122 A1 May 1, 2025

(51) Int. Cl.
*A61M 5/315* (2006.01)
*A61M 5/31* (2006.01)

(52) U.S. Cl.
CPC ...... *A61M 5/31581* (2013.01); *A61M 5/3135* (2013.01); *A61M 2005/31508* (2013.01)

(58) Field of Classification Search
CPC ........... A61M 5/31581; A61M 5/3135; A61M 2005/31508
See application file for complete search history.

(56) References Cited

U.S. PATENT DOCUMENTS

| | | | | |
|---|---|---|---|---|
| 9,821,119 | B2 * | 11/2017 | Felsovalyi | A61M 5/31511 |
| 10,493,484 | B2 * | 12/2019 | Keeney | A61M 5/31511 |
| 10,765,811 | B2 | 9/2020 | Vedrine et al. | |
| 2006/0229568 | A1 * | 10/2006 | Koopman | A61M 5/31511 604/187 |
| 2008/0281274 | A1 | 11/2008 | Rolla | |
| 2017/0290987 | A1 | 10/2017 | Mandaroux et al. | |

FOREIGN PATENT DOCUMENTS

| | | |
|---|---|---|
| JP | 2011024687 A | 2/2011 |

OTHER PUBLICATIONS

International Search Report and Written Opinion, Mail Date Jun. 12, 2024.

* cited by examiner

*Primary Examiner* — Bradley J Osinski
(74) *Attorney, Agent, or Firm* — Sand, Sebolt & Wernow Co., LPA

(57) ABSTRACT

A syringe with an arcuate plunger handle that can conform to either the inside or the outside of the barrel. This ensures that the plunger pushes straight, and in conjunction with the plunger head being hinged allows the handle to be folded onto the outside of the barrel to minimise volume. A rotatable cap attached to the handle covers the dispensing end of the syringe and seals the tip.

10 Claims, 6 Drawing Sheets

SYRINGE WITH A CONFORMABLE HANDLE

FIELD OF THE INVENTION

The present invention relates to a re-usable syringe for non-medical applications such as dispensing food stuffs, in particular a syringe in which the plunger includes a handle conformable to the barrel.

BACKGROUND TO THE INVENTION

Syringes are convenient devices for storing and dispensing many foodstuffs, allowing for accurately controlled dispensing directly into a persons or animals mouth, onto another serving implement, or onto foodstuff.

A conventional syringe design can be used for dispensing foodstuffs, however their design limits their suitability for such, and they are not designed for re-use.

A first issue is that when a syringe is full, the plunger extends from the syringe barrel almost doubling its size and may be inadvertently pushed and dispense the contents of the syringe.

A second issue is that the dispensing end does not have a suitable cap. This is not an issue when the syringe is packaged, but such packaging is usually in the form of a plastic wrapper which is not suitable for re-use. When present caps are separate items and easily lost, again making them unsuitable for re-use. Caps also usually just cover the dispensing tip and not the entire dispensing end. It is desirable to cover the entire dispensing end to keep it clean as it will potentially come in contact with the user's lips or tongue.

A further issue is that to clean a syringe the plunger must be removed from the barrel. This is inconvenient as either the barrel or the plunger may be lost.

Improved syringes with articulated plunges are known, and overcome some of the issues identified, but none are none to solve all issues adequately.

The object of this invention is to provide a syringe to alleviate the above problems, or at least provide the public with a useful alternative.

SUMMARY OF THE INVENTION

In a first aspect the invention provides syringe comprising a barrel with an open end and a dispensing end, and a plunger with a handle and a head, wherein the handle is in the form of an arc and is made of a resilient material such that the plunger can expand or contract to conform to the shape of the barrel.

Preferably an inner surface of the handle conforms with an outer surface of the barrel, and an outer surface of the handle conforms with an inner surface of the barrel.

In preference the arc of the handle is greater than 180 degrees thus allowing the handle to clip onto the barrel.

Preferably the handle is hingedly attached to the head, or the handle may be releasably attached to the head.

Preferably the barrel further comprises an inward lip adjacent the open end, and the head comprises an outer lip that engages with the inner lip to prevent unintentional extraction of the head from the barrel.

In preference the barrel further comprises a dispensing tip at the dispensing end, and the handle further comprises a rotatably mounted cap, the cap rotatable form a first position disengaged from the dispensing end to a second position where the cap covers the dispensing end and seals the dispensing tip.

It should be noted that any one of the aspects mentioned above may include any of the features of any of the other aspects mentioned above and may include any of the features of any of the embodiments described below as appropriate.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DRAWING COMPONENTS

Figure 1A:
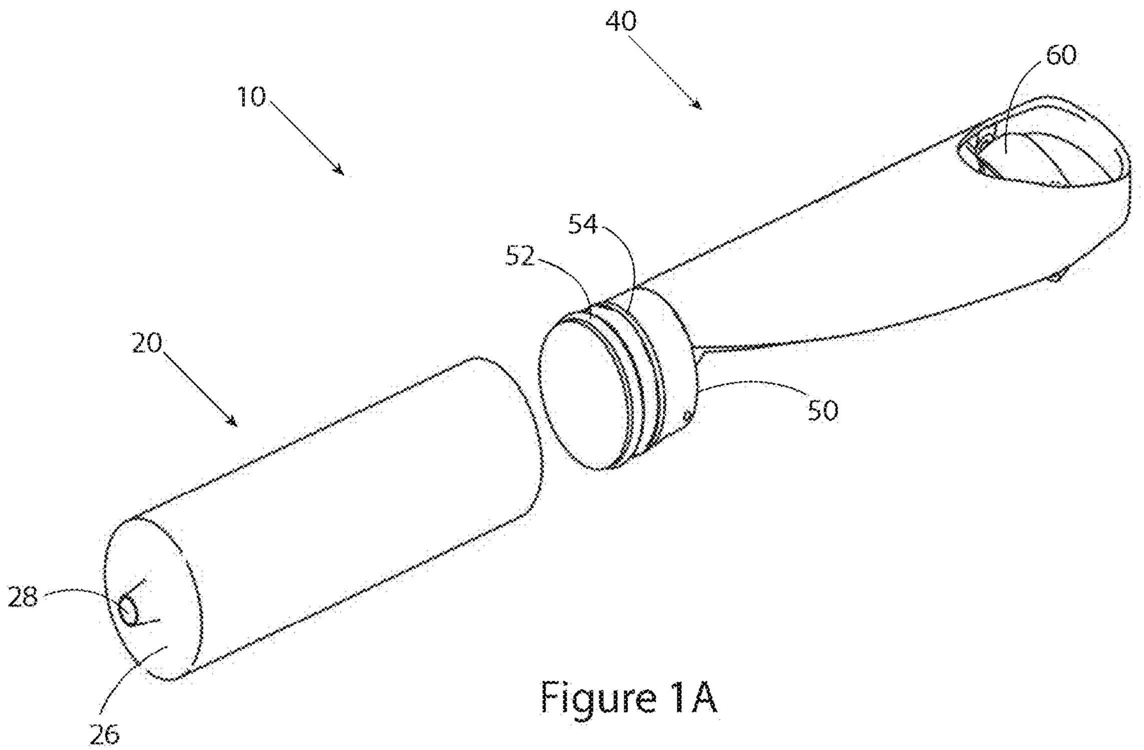
FIGS. 1A and 1B show a disassembled view of a syringe according to a first embodiment of the invention from a first and second viewpoint.

The drawings include the following integers.

10 syringe (first embodiment)
20 barrel
22 body
24 open end
26 dispensing end
28 dispensing tip
30 inner lip
40 plunger
42 handle
44 axle
46 loop
50 head
52 seal
54 outer lip
60 cap
62 sealing strip
140 plunger (second embodiment)
142 handle
143 handle end
145 hooks
150 head
155 loops
200 dishwasher rack

DETAILED DESCRIPTION OF THE INVENTION

The following detailed description of the invention refers to the accompanying drawings. Wherever possible, the same reference numbers will be used throughout the drawings and the following description to refer to the same and like parts.

Dimensions of certain parts shown in the drawings may have been modified and/or exaggerated for the purposes of clarity or illustration.

The present invention provides a re-usable syringe with several features making it suitable for various dispensing applications. It is discussed in the context of storing and dispensing foodstuffs, but it is to be understood that the syringe is suitable for dealing with a large variety of substances, for example paint or silicon. A resilient and arcuate plunger handle can expand and contract to conform to either the inside or the outside of the barrel. This ensures that the plunger pushes straight to prevent leakage past the plunger head, and in conjunction with the plunger head being hinged allows the handle to be folded onto the outside of the barrel to minimise volume. A rotatable cap attached to the handle covers the dispensing end of the syringe and seals the tip. The plunger may also be removed from the barrel and clipped to the outside to keep the two parts together when going through a dishwasher.

Figure 1B:
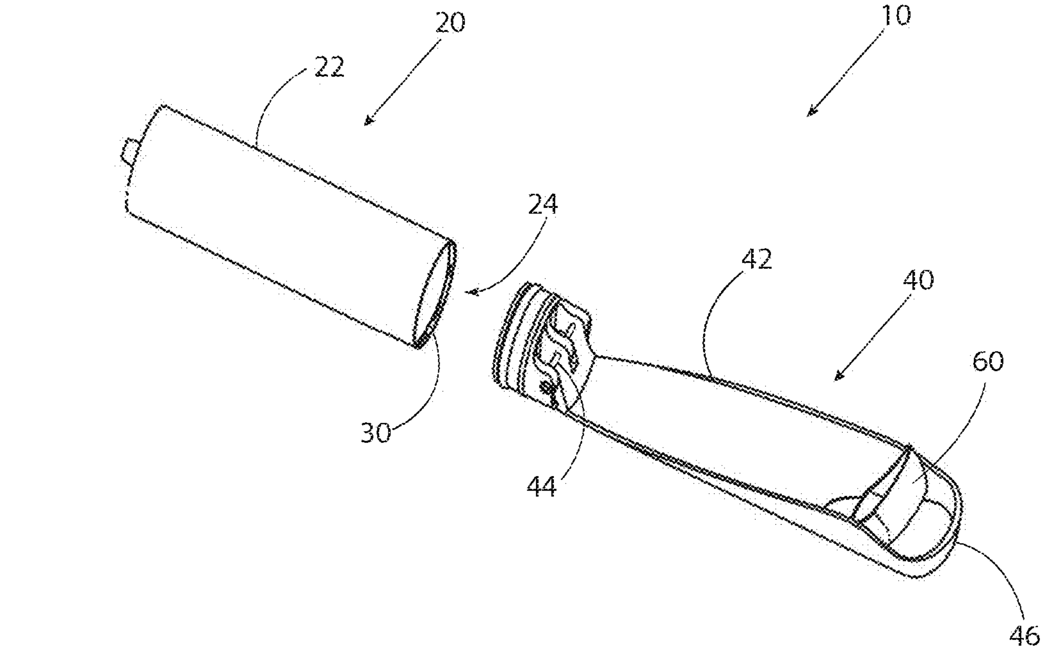

FIGS. 1A and 1B show two different views of a syringe 10 according to a first embodiment of the invention that has been disassembled to allow for identification of the syringes various features. Similar to a conventional syringe, the syringe 10 comprises a barrel 20 with dispensing tip 28, and plunger 40 with a handle 42 and head 50 with seal 52.

The barrel 20 comprises an elongate cylindrical body 22 with an open end 24 and dispensing end 26 with dispensing tip 28. An inner lip 30 helps to prevent the plunger 40 from being inadvertently fully dislodged from the barrel.

The plunger 40 is very distinct from conventional syringe plungers and comprises an elongate arcuate handle 42. The handle is made from a resilient material so it can expand or contract in diameter, allowing the inner surface of the handle to conform with the outer surface of the barrel body 22, and also allowing the outer surface of the handle to conform with the inner surface of the barrel body 22. A cap 60 is pivotally mounted to the handle 42 and is used to cover the dispensing end 26 of the barrel 20 and seal the dispensing tip 28. As seen in FIG. 3B, the cap 60 includes a sealing strip 62, made of a flexible material such as silicone, that is held against the end of the dispensing tip 28 when the cap is in place to ensure a good seal of the dispensing tip. The handle 42 is pivotally attached to the head 50 by axle 44 allowing the handle to rotate whilst the head 50 is inside the barrel 20 as discussed below in relation to FIGS. 2A to 2C. The head further includes outer lip 54 which engages with inner lip 30 of the barrel 20 to further prevent the plunger 40 from being inadvertently fully dislodged from the barrel. A loop 46 at the end of the handle serves many functions as well as making the syringe easy to carry and allowing it to be attached to another object. The loop is needed to get enough force to suck in viscous liquids such as yogurts and soups into the syringe. The loop is comfortable and easy to hold while pushing the handle to dispense foodstuffs. The loop also plays an important role in allowing flexibility of the handle to fit in the barrel while keeping the handle rigid enough.

Figure 2A:
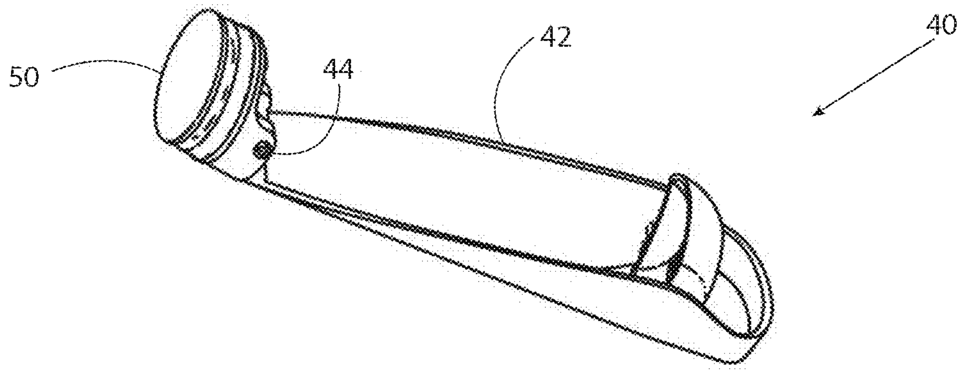
FIGS. 2A to 2C show the plunger of the syringe in isolation and how it folds.
Figure 2B:
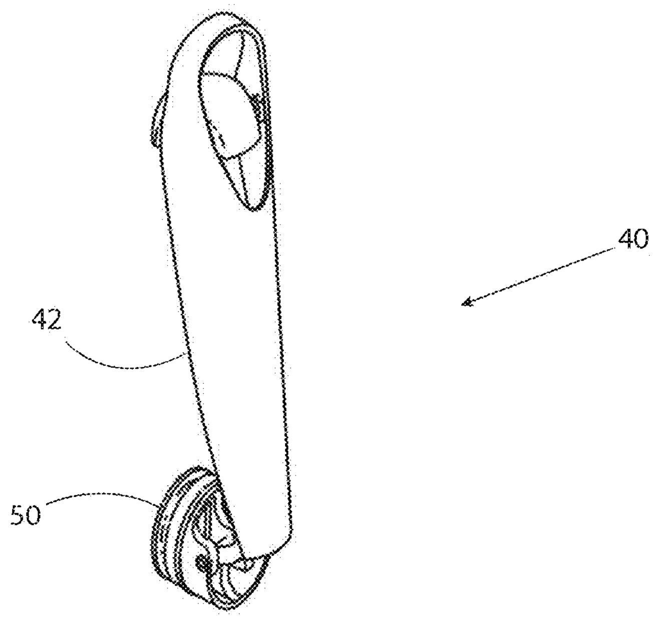
Figure 2C:
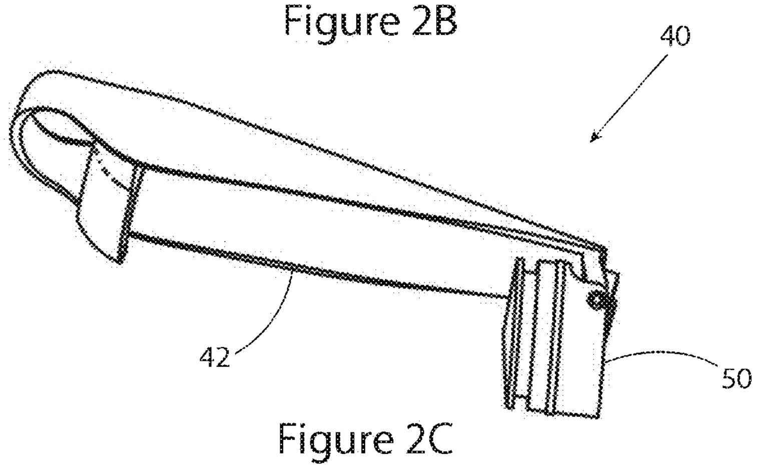

FIG. 2A to 2C show the plunger 40 in isolation and display how the handle 42 can rotate through 180 degrees with respect to the head 50. The configuration of FIG. 2A allows the handle 42 (and attached head 50) to be inserted into or retracted from the barrel 20, and the configuration of FIG. 2C allows the handle 42 to conform to the outside of the barrel 20 and the cap 60 to cover the dispensing end 26 of the barrel and seal the dispensing tip 28.

Figure 3A:
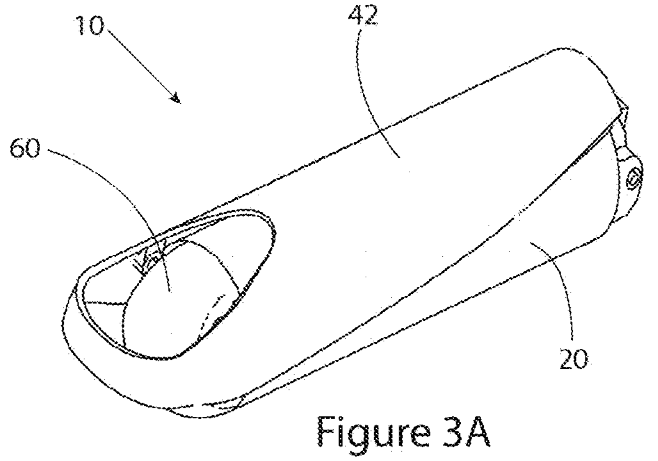
FIGS. 3A to 3C show three different configurations of the syringe in use.
Figure 3B:
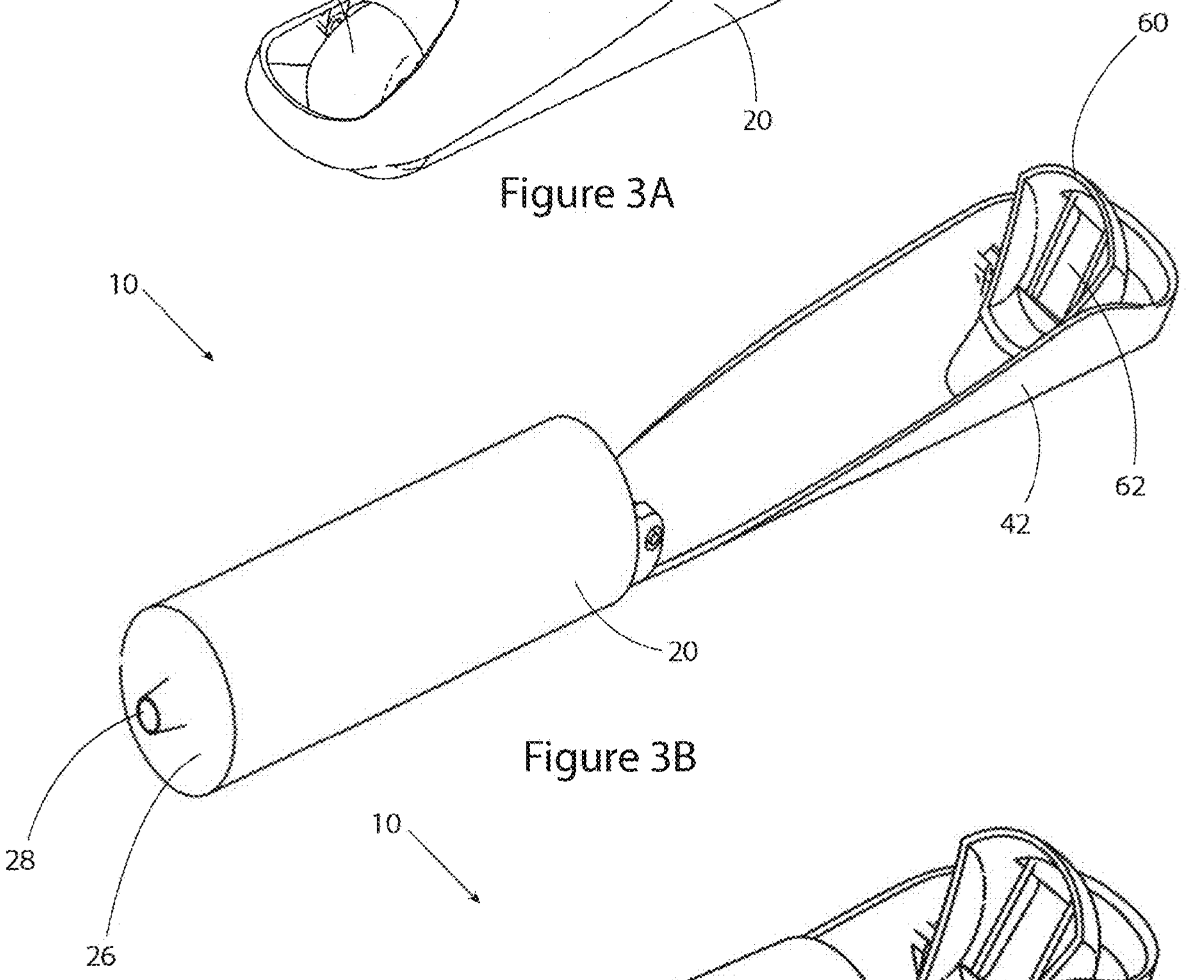

FIGS. 3A to 3B show the complete syringe 10 in use. In all three Figures the head 50 of the plunger 40 is inside the barrel 20 and thus obscured.

FIG. 3A shows the syringe 10 in a closed configuration in which the handle 42 is engaged with the outer surface of the barrel 20 and effectively clips around the barrel 20 keeping the handle in place. The cap 60 covers the dispensing end 26 of the barrel and seals dispensing tip 28 thus preventing unintentional discharge of the barrel contents and keeping the dispensing end and tip clean. In this configuration the head 50 of the plunger 20 is adjacent the non-dispensing end of the barrel, and the barrel may be empty or full of foodstuff for dispensing. The closed configuration is particularly compact allowing the syringe to be easily stowed or carried without the danger of leakage or unintentional dispensing.

Figure 3C:
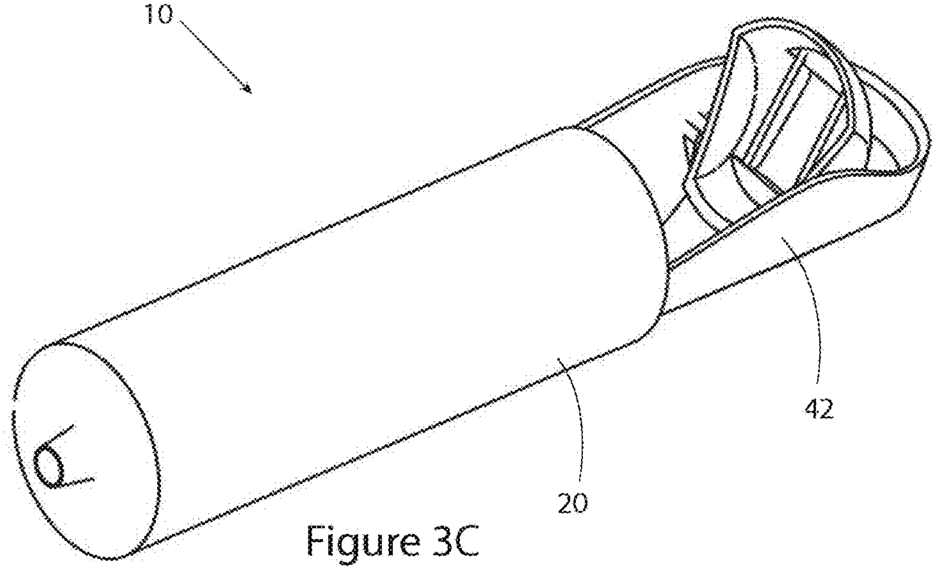

FIG. 3B shows the syringe 10 in an open retracted configuration which is reached from the closed configuration of FIG. 3A by rotating the handle 20. The handle can then be pushed into the barrel 20 to reach the open extended configuration of FIG. 3C. As the handle is pushed into the barrel it contracts in diameter such that its outer diameter matches the inner diameter of the barrel. If foodstuff is present, it will be pushed towards the dispensing end 26 by the attached head 50 and discharged via the dispensing tip 28. Retracting the handle again until it reaches the open retracted configuration of FIG. 3B will allow the handle to be rotated back to the closed configuration of FIG. 3A. The movement from FIG. 3C to FIG. 3B can be used to fill the syringe with food stuff by sucking it through the dispensing tip 28. This is particularly suitable for filling the syringe with liquids. For viscous liquids or soft solids, the plunger can be completely removed from the barrel, as per FIG. 1A or 1B, and placed into the syringe via the non-dispensing end.

Figure 4A:
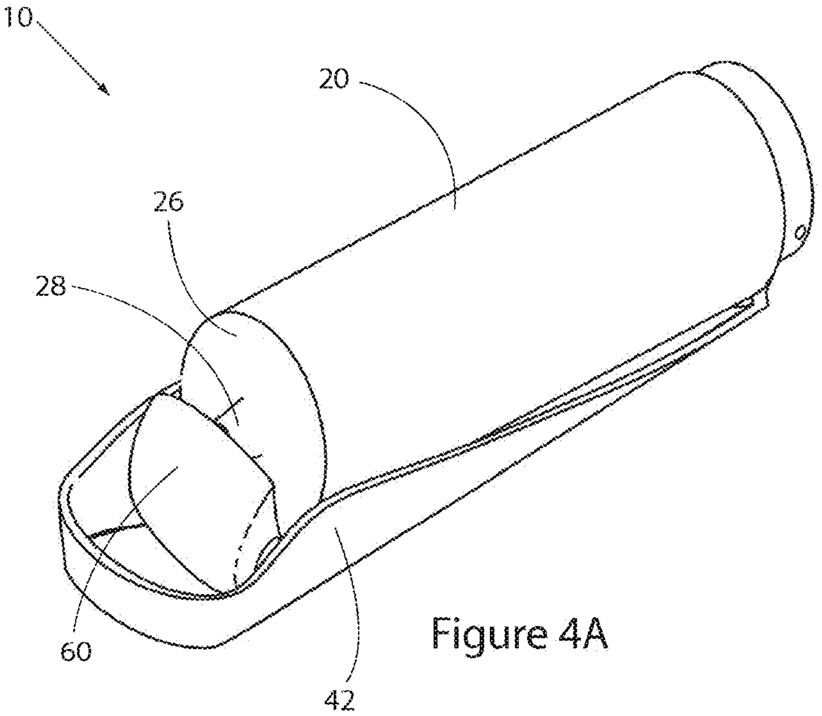
FIGS. 4A and 4B show how the cap of the syringe operates.
Figure 4B:
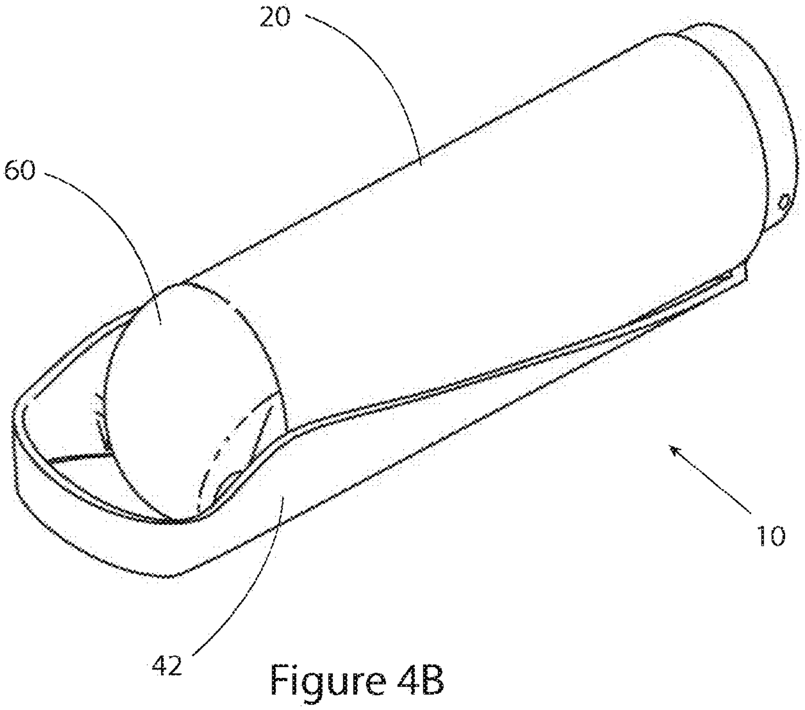

FIGS. 4A and 4B show how the cap 60 engages/disengages with the barrel 20. In FIG. 4A the handle 42 is rotating upwards to come in contact with the barrel 20. As it does so, the cap 60 rotates within the handle until it covers the dispensing end 26 of the barrel as per FIG. 4B, and the sealing strip 62 in the cap (as seen in FIG. 3B) comes in contact with the end of the dispensing tip 28.

Figure 5:
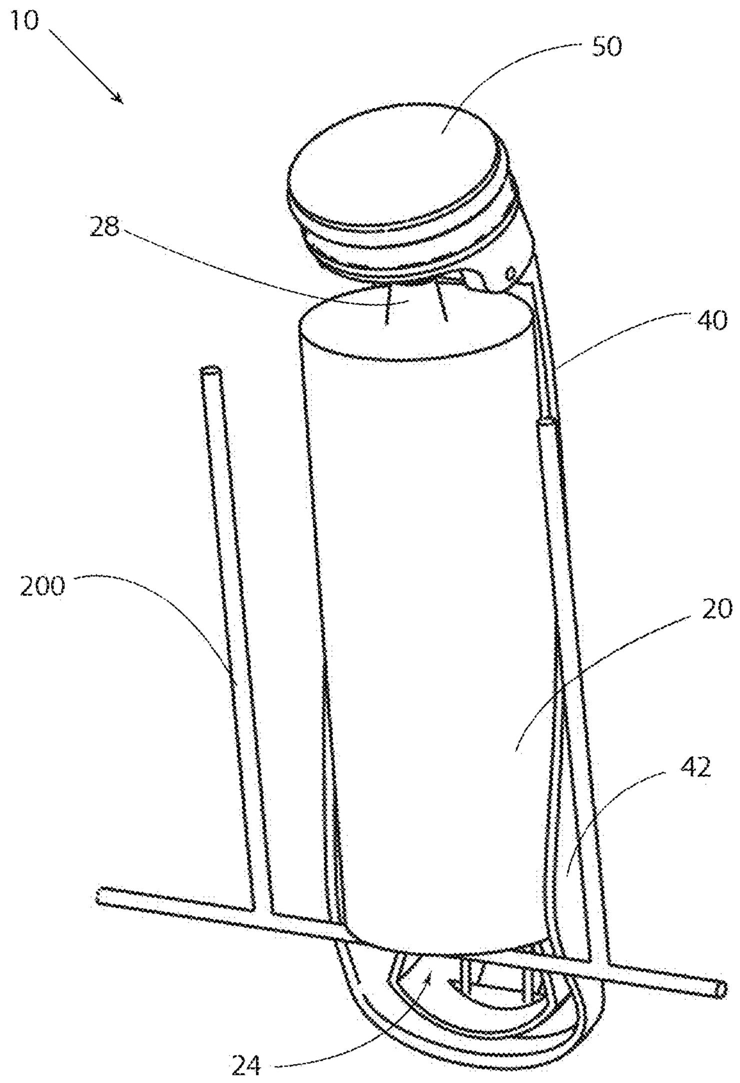
FIG. 5 shows the syringe in a dishwashing configuration.

FIG. 5 shows the syringe 10 in a dishwashing configuration. The plunger has been completely taken out of the barrel 20, rotated through 180 degrees and the handle 42 clipped onto the outside of the barrel. The syringe can then be placed on a dishwashing rack 200, supported by a prong of the dishwashing rack entering into the barrel 20 via the open dispensing end 24. The inside of the barrel, the tip and the head are all exposed to the dishwashing environment whilst being conveniently held together.

Figure 6A:
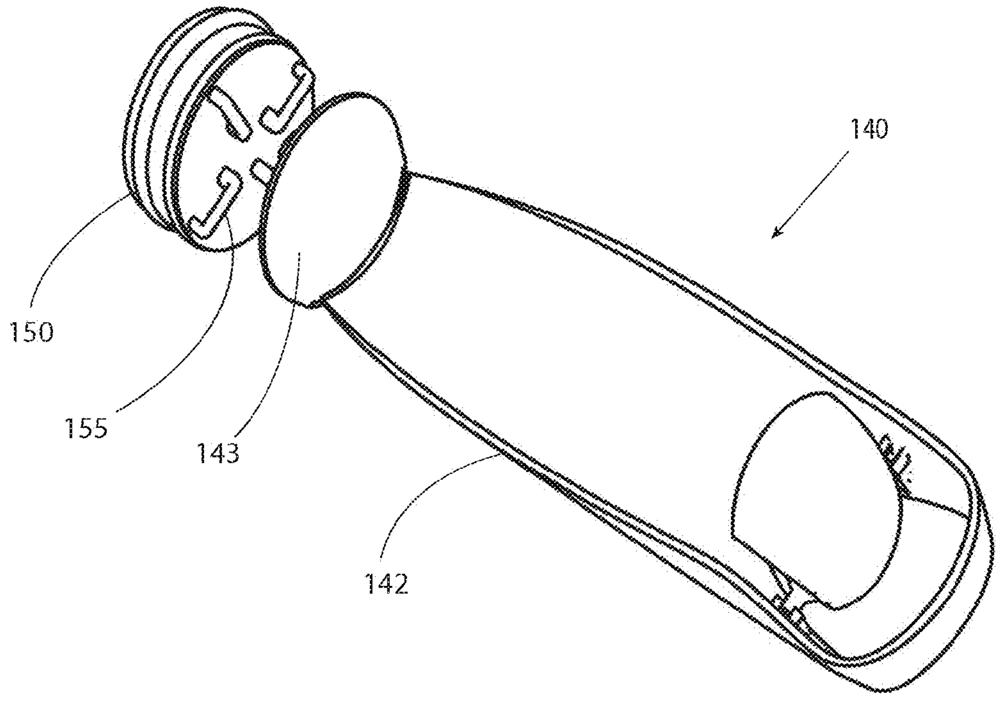
FIGS. 6A and 6B show a second embodiment of the plunger of the syringe in which the handle is detachable from the head.
Figure 6B:
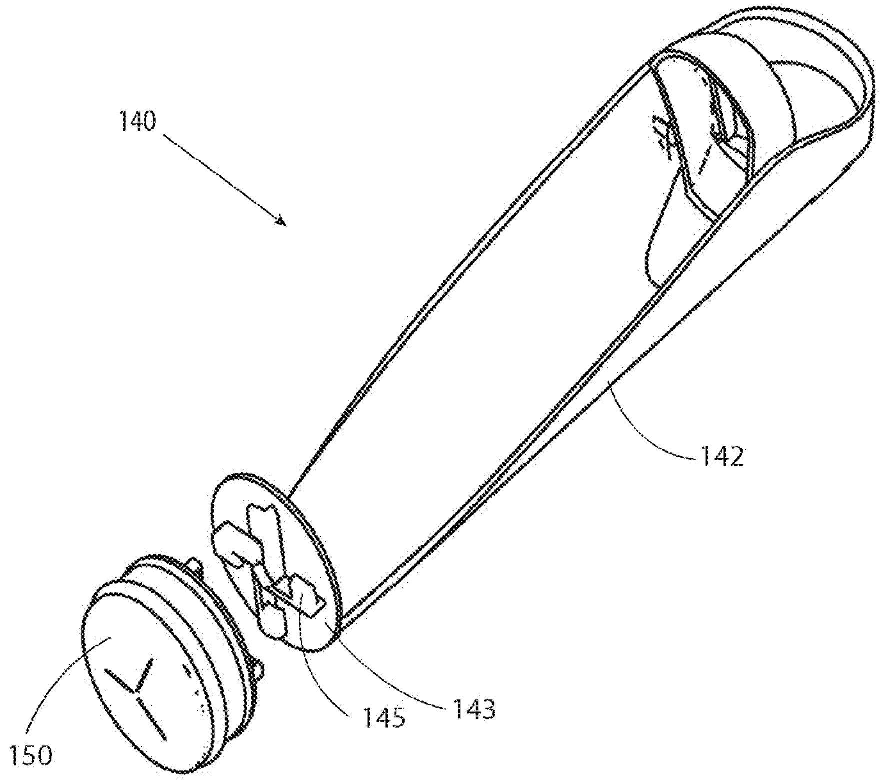

FIGS. 6A and 6B show a second embodiment of a plunger 140 in which the handle 142 is readily detachable from the head 150 by the user. This is useful when the syringe has only had a portion of its contents dispensed as the head 150 can stay in contact with the barrel contents, and the syringe place into a closed configuration, as per FIG. 3A. The head 150 includes a series of loops 155 which engage with hooks 145 on the handle end 143. To engage or disengage the head 150 and handle 140, the handle is simply rotated in one direction or the other.

The reader will now appreciate the present invention which provides a syringe with an arcuate plunger handle that can conform to either the inside or the outside of the barrel. This ensures that the plunger pushes straight, and in conjunction with the plunger head being hinged allows the handle to be folded onto the outside of the barrel to minimise volume. A rotatable cap attached to the handle covers the dispensing end of the syringe and seals the tip.

Further advantages and improvements may very well be made to the present invention without deviating from its scope. Although the invention has been shown and described in what is conceived to be the most practical and preferred embodiment, it is recognized that departures may be made therefrom within the scope of the invention, which is not to be limited to the details disclosed herein but is to be accorded the full scope of the claims so as to embrace any and all equivalent devices and apparatus. Any discussion of the prior art throughout the specification should in no way be considered as an admission that such prior art is widely known or forms part of the common general knowledge in this field.

In the present specification and claims (if any), the word "comprising" and its derivatives including "comprises" and "comprise" include each of the stated integers but does not exclude the inclusion of one or more further integers.

The invention claimed is:

1. A syringe comprising:

a barrel with an open end and a dispensing end;

a plunger with a handle and a head;

wherein the handle has a proximate end and a distal end opposite and spaced apart from one another;

wherein the handle is in the form of an arc to conform to a shape of the barrel;

wherein the arc at the proximate end is less than 180 degrees; and wherein an inner surface of the handle conforms with an outer surface of the barrel.

2. The syringe as in claim 1, wherein the arc of the handle at the distal end is greater than 180 degrees thus allowing the handle to clip onto the barrel.

3. The syringe as in claim 1, wherein an outer surface of the handle conforms with an inner surface of the barrel.

4. The syringe as in claim 1, wherein the handle is hingedly attached to the head.

5. The syringe as in claim 1, wherein the handle is releasably attached to the head.

6. The syringe as in claim 1, wherein the barrel further comprises an inward lip adjacent the open end, and the head comprises an outer lip that engages with the inner lip to prevent unintentional extraction of the head from the barrel.

7. The syringe as in claim 1, wherein the barrel further comprises a dispensing tip at the dispensing end, and the handle further comprises a rotatably mounted cap, the cap rotatable from a first position disengaged from the dispensing end to a second position where the cap covers the dispensing end and seals the dispensing tip.

8. The syringe as in claim 1, wherein the handle is configured to be inserted or retracted from an interior of the barrel.

9. The syringe as in claim 1, wherein the barrel and handle are configured to remain engaged with one another during the use and storage of the syringe.

10. The syringe as in claim 1, wherein the handle is made of a resilient material such that the plunger can expand or contract to conform to the shape of the barrel.

* * * * *